United States Patent
Pak

(10) Patent No.: US 10,604,497 B2
(45) Date of Patent: Mar. 31, 2020

(54) SILVER IMPREGNATION METHOD FOR PRODUCING ETHYLENE OXIDE CATALYST WITH ENHANCED CATALYTIC ABILITY

(71) Applicant: SCIENTIFIC DESIGN COMPANY INC., Little Ferry, NJ (US)

(72) Inventor: Serguei Pak, Teaneck, NJ (US)

(73) Assignee: SCIENTIFIC DESIGN COMPANY INC., Little Ferry, NJ (US)

( * ) Notice: Subject to any disclaimer, the term of this patent is extended or adjusted under 35 U.S.C. 154(b) by 0 days.

(21) Appl. No.: 15/873,125

(22) Filed: Jan. 17, 2018

(65) Prior Publication Data
US 2018/0201595 A1    Jul. 19, 2018

Related U.S. Application Data

(60) Provisional application No. 62/447,043, filed on Jan. 17, 2017.

(51) Int. Cl.
- *C07D 301/10* (2006.01)
- *B01J 23/66* (2006.01)
- *C01G 5/00* (2006.01)

(52) U.S. Cl.
CPC ............ *C07D 301/10* (2013.01); *B01J 23/66* (2013.01); *C01G 5/00* (2013.01); *C01P 2004/03* (2013.01); *C01P 2004/64* (2013.01); *Y02P 20/52* (2015.11)

(58) Field of Classification Search
CPC .................................................. C07D 301/10
USPC ....................................................... 549/534
See application file for complete search history.

(56) References Cited

U.S. PATENT DOCUMENTS

| | | | |
|---|---|---|---|
| 5,281,728 A * | 1/1994 | Wunde .................... | B01J 23/50 549/534 |
| 5,504,053 A * | 4/1996 | Chou ....................... | B01J 23/68 502/208 |
| 8,450,236 B2 * | 5/2013 | Fu ............................ | B01J 37/16 502/243 |
| 2016/0251326 A1 * | 9/2016 | Suchanek ............... | B01J 23/688 549/534 |
| 2016/0354760 A1 | 12/2016 | Suchanek | |

FOREIGN PATENT DOCUMENTS

| | | |
|---|---|---|
| CA | 2981009 A1 | 9/2016 |
| RU | 2045335 C1 | 10/1995 |
| WO | 2011146421 A2 | 11/2011 |

OTHER PUBLICATIONS

International Search Report dated May 17, 2018 issued in PCT/US2018/013769.

* cited by examiner

*Primary Examiner* — Nizal S Chandrakumar
(74) *Attorney, Agent, or Firm* — Scully Scott Murphy and Presser

(57) ABSTRACT

A method for producing a catalyst effective in the oxidative conversion of ethylene to ethylene oxide, the method comprising: (i) impregnating a porous refractory carrier with a sub-catalytic level of silver ion in a range of 0.1 wt % to 1 wt % of silver by weight of the carrier and silver, and at least partially reducing said silver ion to elemental silver to produce a low-silver catalyst precursor having isolated silver atoms or silver nanoparticles on surfaces of said refractory carrier; and (ii) further impregnating the low-silver catalyst precursor with a catalytic amount of silver ion of at least 10 wt % total amount of silver and at least one promoting species by weight of the carrier and silver, and subjecting the further impregnated carrier to an elevated temperature of at least 200° C. to completely reduce silver ion to elemental silver in the carrier. The low-silver catalyst precursor produced in step (i) is also described in detail. Methods for using the catalyst produced in step (ii) for the oxidative conversion of ethylene to ethylene oxide are also described.

20 Claims, 2 Drawing Sheets

SILVER IMPREGNATION METHOD FOR PRODUCING ETHYLENE OXIDE CATALYST WITH ENHANCED CATALYTIC ABILITY

CROSS REFERENCE TO RELATED APPLICATIONS

This application is related to and claims the benefit of U.S. Provisional Patent Application Ser. No. 62/447,043 filed Jan. 17, 2017 the entire contents of which are incorporated by reference herein.

FIELD OF THE INVENTION

The present disclosure relates to silver-based ethylene oxide catalysts for the oxidative conversion of ethylene to ethylene oxide, and in particular, to their preparation. More particularly, the present disclosure relates to methods for producing silver-based ethylene oxide catalysts having an improved activity, selectivity, or stability by virtue of the methodology involved in impregnating the carrier with silver and one or more promoting species.

BACKGROUND

As known in the art, high selectivity catalysts (HSCs) for the epoxidation of ethylene refer to those catalysts that possess selectivity values higher than high activity catalysts (HACs) used for the same purpose. Both types of catalysts include silver as the active catalytic component on a refractory support (i.e., "carrier", such as alumina). Typically, one or more promoters are included in the catalyst to improve or adjust properties of the catalyst, such as selectivity.

Generally, HSCs achieve the higher selectivity (typically, in excess of 87 mole %) by incorporation of rhenium as a promoter. Typically, one or more additional promoters selected from alkali metals (e.g., cesium), alkaline earth metals (e.g., strontium), transition metals (e.g., tungsten compounds), and main group elements (e.g., sulfur and/or halide compounds) are also included.

There are also ethylene epoxidation catalysts that may not possess the selectivity values typically associated with HSCs, although the selectivity values are improved over HACs. These types of catalysts can also be considered within the class of HSCs, or alternatively, they can be considered to belong to a separate class, e.g., "medium selectivity catalysts" or "MSCs." These types of catalysts may exhibit selectivities of at least 83 mole % and up to 87 mole %. In contrast to HSCs and MSCs, HACs are ethylene epoxidation catalysts that generally do not include rhenium, and for this reason, do not provide the selectivity values of HSCs or MSCs. Typically, HACs include cesium (Cs) as the only promoter.

For all of these types of catalysts, there remains a need to improve the activity and selectivity performance. Moreover, it is well known that with use of a catalyst, the catalyst will age (i.e., degrade) until use of the catalyst is no longer practical, i.e., when activity and selectivity values diminish to a level that is no longer industrially efficient or economical. Thus, there is a further continuous need to extend the useful lifetime (i.e., "longevity" or "usable life") of these catalysts by maintaining an effective level of activity and selectivity characteristics. The useful lifetime of the catalyst is directly dependent on the stability of the catalyst. As used herein, the "useful lifetime" is the time period for which a catalyst can be used until one or more functional parameters, such as selectivity or activity, degrade to such a level that use of the catalyst becomes impractical. Although many approaches for boosting the activity, selectivity, or stability of the catalyst have been undertaken, there remains a need for further improvements and a more straight-forward and cost-effective method for achieving such an improved catalyst.

SUMMARY

The present disclosure is foremost directed to a method of impregnating a carrier with silver in a manner that results in an improved activity, selectivity, or stability in the resulting catalyst compared to conventional impregnation methods of the art. More particularly, the method employs a two-stage silver impregnation process in which a sub-catalytic level of silver (e.g., up to or less than 1 wt %) is deposited on a carrier such that the carrier contains isolated atoms or nanoparticles of elemental silver deposited on its surface, followed by impregnation with additional silver to bring the silver content on the carrier to a catalytically effective level of silver (e.g., at least 10 wt %) along with deposition of one or more promoting species.

In particular embodiments, the method includes the following steps: (i) impregnating a porous refractory carrier with a sub-catalytic level of silver ion in a range of 0.01 wt % to 1 wt % of silver per total weight of the refractory carrier and silver, and subjecting the refractory carrier having a sub-catalytic level of silver ion to conditions under which silver ions become at least partially reduced to elemental silver to produce a low-silver catalyst precursor having isolated silver atoms or silver nanoparticles deposited on surfaces of the refractory carrier; and (ii) impregnating the low-silver catalyst precursor with a catalytic amount of silver ion of at least 10 wt % total amount of silver per total weight of the refractory carrier and silver, and also impregnating the low-silver catalyst precursor with at least one inorganic promoting species that promotes the oxidative conversion of ethylene to ethylene oxide and that is included in a catalytically promoting amount, and subjecting the refractory carrier having a catalytic level of silver ion, as produced in step (ii), to a calcination process in which the refractory carrier having a catalytic level of silver ion is subjected to an elevated temperature of at least 200° C. to reduce silver ion to elemental silver in the refractory carrier. The resulting catalyst effectively converts ethylene to ethylene oxide under conditions commonly practiced in the art, and moreover, may be an HSC, HAC, or MSC type of catalyst. The catalyst exhibits an improved performance compared to a catalyst prepared using a conventional single-stage impregnation process, using the same total amount of silver and under equivalent operating conditions.

Notably, the catalyst, as produced in step (ii), has herein been found to possess a greater coverage (deposition) of the at least one inorganic promoting species on the elemental silver deposited on the carrier, compared to a conventional process in which a catalyst is produced by impregnating the refractory carrier with a catalytic amount of silver ion of at least 10 wt % along with at least one inorganic promoting species in a single impregnation step, without step (i), followed by calcination at an elevated temperature of at least 200° C. Without being bound by theory, it is believed that the greater coverage of promoters on silver provided by the presently described method results in a higher concentration of active sites, which results in the improved performance.

BRIEF DESCRIPTION OF THE FIGURES

FIG. 1A is an SEM (scanning electron microscopy) image of an alumina carrier before any deposition of silver. FIG. 1B is an SEM image of the alumina carrier after deposition of 0.18 wt % silver, as described in Example 2. The SEM images were taken at 30KX magnification.

FIG. 2A is an SEM image of the HSC catalyst prepared in Example 1 prepared by single-step deposition of silver and promoters, with total deposited silver of 16.3 wt %. FIG. 2B is an SEM image of the HSC catalyst prepared in Example 2 after a first low silver impregnation followed by a second (conventional) silver impregnation with silver and promoters, with total deposited silver of 16.6 wt %. The SEM images were taken at 30KX magnification.

DETAILED DESCRIPTION

Figure 1A:
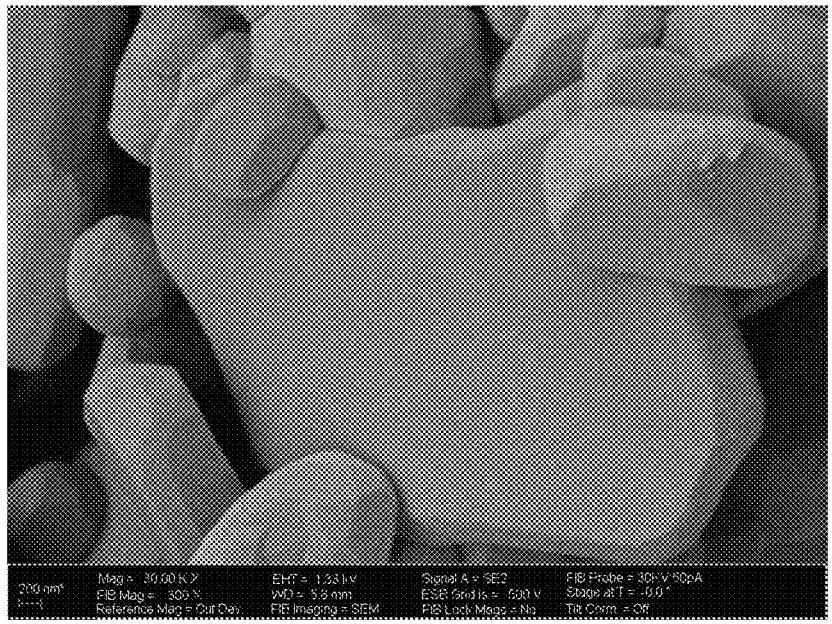
FIGS. 1A, 1B.

In the method for producing the catalyst, a two-stage impregnation process is employed wherein, in a first impregnation stage, a sub-catalytic level of silver (e.g., up to or less than 1 wt %) is deposited onto a porous refractory carrier (i.e., "carrier") such that the carrier contains isolated atoms or nanoparticles of elemental silver deposited on its surface, followed by a second impregnation stage in which the carrier is impregnated with additional silver sufficient to bring the silver content on the carrier to a catalytic level of silver (e.g., at least 10 wt %) along with deposition of one or more promoting species. The term "isolated," as used herein, indicates that the atoms or nanoparticles of elemental silver (primary or secondary aggregated particles, typically of no more than 10 nm dimension) are not aggregated as particles larger than 10 nm, 20 nm, or 50 nm. In some embodiments, the majority of silver atoms or nanoparticles are not in physical contact with each other. The resulting catalyst exhibits an improvement in at least one of an improved catalyst activity, selectivity, and stability, compared to a catalyst produced in a conventional manner by impregnating the refractory carrier with a catalytic amount of silver ion of at least 10 wt % and at least one inorganic promoting species in a single impregnation step (i.e., without the preliminary deposition of silver nanoparticles), followed by calcination.

The first impregnation stage is achieved by impregnating the carrier with a sub-catalytic amount of silver ion within a range of about or at least 0.01 wt % and up to or less than 1 wt % of silver by total weight of the carrier, and subjecting the carrier with the sub-catalytic amount of silver ion to conditions under which the silver ions are at least partially reduced to zerovalent silver, and specifically, atoms or nanoparticles of zerovalent silver, wherein a portion of the atoms of silver may or may not be in the form of ionic silver, or the atoms of silver may all be zerovalent silver atoms; and wherein the nanoparticles (which may include clusters) of silver may or may not contain ionic silver, or may be composed solely of zerovalent silver. Some atomically deposited silver can also be present in the ionic state. Any of the reduction methods well known in the art may be employed for reduction of the silver ions, such as by contact with a chemical reducing agent, such as oxalate, citrate, hypophosphite, borohydride, reducing sugar, aldehyde, or polyol. The reduction of the silver ions may also be conducted at ambient temperature (e.g., 15° C.-30° C. or about 20° C. or 25° C.) or at an elevated temperature. The elevated temperature may be about, at least, or up to, for example, 50° C., 100° C., 150° C., 200° C., or 250° C., or within a range of any of the foregoing temperatures. The elevated temperature may function to, for example, evaporate solvent absorbed into the carrier from the impregnation, and possibly also to encourage the reduction process and deposition of silver in a highly dispersed state. The temperature may also be any of the higher temperatures commonly employed for calcining a silver-impregnated precursor carrier to produce a catalytically active silver catalyst. Other conditions commonly employed during calcination, such as a modified reaction pressure, may be employed during the reduction step.

The silver nanoparticles deposited on surfaces of the carrier in the first impregnation stage generally have a size (i.e., diameter or longest dimension) no larger than 100 nm, and more typically up to or less than 50 nm, 20 nm, 10 nm, 5 nm, 4 nm, 3 nm, 2 nm, or 1 nm. The term "silver nanoparticles," as used herein, is also meant to encompass "silver nanoclusters," which may contain a small number (e.g., 3-100) of silver atoms. Although the larger varieties of silver nanoclusters may have sizes overlapping those of the nanoparticles, the smaller varieties of silver nanoclusters may have sizes less than 1 nm, e.g., up to or less than 0.8, 0.7, 0.6, or 0.5 nm. In some embodiments, the majority (i.e., more than 50% or at least 60%) of the deposited silver is in the form of isolated nanoparticles, or in the form of isolated nanoclusters having a size below 1 nm, or in the form of isolated atoms, or a combination thereof.

The amount of silver incorporated into the carrier in the first impregnation stage (i.e., the sub-catalytic amount of silver) should be low enough to result in the deposition of isolated atoms and/or nanoparticles of silver. In different embodiments, the sub-catalytic amount of silver ion corresponds to an amount of silver ion of about 0.01, 0.05, 0.1, 0.2, 0.3, 0.4, 0.5, 0.6, 0.7, 0.8, 0.9 or 1 wt %, or an amount within a range bounded by any two of the foregoing values, e.g., 0.01-1 wt %, 0.05-1 wt %, 0.1-1 wt %, or an amount of at least or above any of the foregoing values and less than 1 wt %. The amount of silver ion impregnated in the carrier in the first impregnation stage necessarily results in an equivalent amount of silver atoms and/or nanoparticles incorporated into the resulting low-silver catalyst precursor produced after the elevated temperature treatment. The low weight percentages of silver incorporated into the carrier, as provided above, generally correspond to a silver distribution of at least 1, 5, 10, 20, 30, 40, or 50 µmol/m$^2$ (i.e., micromoles per square meter) and up to 100, 150, 200, or 250 µmol/m$^2$, or a distribution within a range bounded by any two of the foregoing values.

Moreover, the terms "deposited in" and "deposited on" are herein considered synonymous, since the silver will necessarily reside on both outer (external) surfaces and inner (interior pore) surfaces of the carrier. For this reason, the instant disclosure refers to deposition of silver on "surfaces," which refer to both inner and outer surfaces of the carrier. The instant disclosure also uses the term "incorporated into" when referring to the deposition of silver on the carrier since silver will necessarily be deposited on all surfaces of the carrier, including interior surfaces.

In some cases, the silver nanoparticles may have clearly delineated edges or facets, while in other cases the silver nanoparticles may appear as amorphous isolated islands of nanoscale dimension of silver. The isolated nanoparticles may be primary nanoparticles or an agglomeration of nanoparticles, wherein the agglomerates, if present, are of nanoscale dimension, as provided above. In some embodiments, at least a portion of the silver deposited in the low-silver catalyst precursor is in the form of isolated nanoparticles, i.e., there may or may not also exist areas of deposited silver not in the form of isolated nanoparticles. In other embodiments, at least 50%, 60%, 70%, 80%, 90%, 95%, or 100% (all) of the deposited silver in the low-silver catalyst precursor is in the form of isolated silver nanoparticles. In further embodiments, at least a portion or all of the silver may be deposited as a monolayer or sub-monolayer of silver atoms or nanoparticles in the low-silver catalyst precursor.

The low-silver catalyst precursor, produced as described above, is then treated by a second stage of impregnation with silver to bring the total amount of silver deposited in the carrier to a catalytically effective amount of silver. More specifically, in the second impregnation stage, the low-silver catalyst precursor, as produced in the first stage, is impregnated with a catalytic amount of silver ion of at least 10 wt % total amount of silver per total weight of the refractory carrier. In different embodiments, the total amount of silver deposited in the carrier in the second impregnation stage is about, at least, or above 10, 12, 15, 18, 20, 22, 25, 28, or 30 wt % of silver by total weight of the carrier and silver.

The carrier having a catalytic level of silver ion is then subjected to a calcination process in which the carrier having a catalytic level of silver ion is subjected to an elevated temperature of at least 200° C. to reduce silver ion to elemental silver in the carrier. In different embodiments, the elevated temperature in the calcination process is a temperature of at least or above 200° C., 250° C., or 300° C., and up to or less than 350° C., 400° C., 450° C., 500° C., 550° C., or 600° C., or a temperature within a range bounded by any two of the foregoing temperatures, e.g., 200° C.-600° C. The reaction pressure during the elevated temperature step may be ambient (e.g., about 1 atm or 1 bar), or an elevated pressure, such as 5, 10, 20, 30, or 40 atm. In the second stage impregnation, the low-silver catalyst precursor is also impregnated with at least one inorganic promoting species that promotes the oxidative conversion of ethylene to ethylene oxide and that is included in a catalytically effective promoting amount. Any of the conditions employed in the calcination process in the first impregnation stage may also be independently employed in the second impregnation stage.

In both the first and second impregnation stages, the impregnation process is conducted according to well-known procedures for impregnating a carrier with silver, except that the first impregnation stage departs from conventional impregnation processes by employing an amount of silver well below the minimum amount known to result in an effective catalyst for the conversion of ethylene to ethylene oxide. The second impregnation stage can be conducted precisely according to the well known and conventional procedures for impregnating a carrier with silver. In both stages, the impregnation is generally accomplished by contacting the carrier with a solution containing silver ion under conditions where the silver-containing solution absorbs or infuses into (i.e., impregnates) the carrier. In the conventional process, as used in the second stage, the carrier is typically impregnated with a solution containing silver ion and one or more inorganic promoting species (i.e., promoters). The silver-containing solution can be made to absorb (impregnate) into the carrier by any of the conventional methods known in the art, e.g., by excess solution impregnation (immersion), incipient wetness impregnation, spray coating, and the like. Typically, the carrier material is placed in contact with the silver-containing solution until a sufficient amount of the solution is absorbed by the carrier. In some embodiments, the quantity of the silver-containing solution used to impregnate the carrier is no more than is necessary to fill the pore volume of the carrier. Infusion of the silver-containing solution into the carrier can be aided by application of a vacuum. For each of the first and second impregnation stages, a single impregnation or a series of impregnations, with or without intermediate drying, may be used, depending in part on the concentration of the silver component in the solution. However, the present invention generally employs a single impregnation step in each of the first and second impregnation stages. Impregnation procedures are described in, for example, U.S. Pat. Nos. 4,761, 394, 4,766,105, 4,908,343, 5,057,481, 5,187,140, 5,102,848, 5,011,807, 5,099,041 and 5,407,888, all of which are incorporated herein by reference. Known procedures for pre-deposition, co-deposition, and post-deposition of the various promoters can also be employed.

The silver-containing solution contains silver in ionic form, generally in the form of a silver compound, complex, or salt, dissolved in a suitable solvent. Silver compounds useful for impregnation include, for example, silver oxalate, silver nitrate, silver oxide, silver carbonate, a silver carboxylate, silver citrate, silver phthalate, silver lactate, silver propionate, silver butyrate and higher fatty acid salts and combinations thereof. A wide variety of complexing or solubilizing agents may be employed to solubilize silver to the desired concentration in the impregnating medium. Useful complexing or solubilizing agents include amines, ammonia, lactic acid and combinations thereof. For example, the amine can be an alkylene diamine having from 1 to 5 carbon atoms. In a preferred embodiment, the solution comprises an aqueous solution of silver oxalate and ethylenediamine. As well known in the art, the complexing/solubilizing agent may be present in the impregnating solution in an amount from about 0.1 to about 5.0 moles of ethylene diamine per mole of silver, preferably from about 0.2 to about 4.0 moles, and more preferably from about 0.3 to about 3.0 moles of ethylene diamine for each mole of silver.

The silver solution can contain any suitable solvent. The solvent can be, for example, water-based, organic, or a combination thereof. In some embodiments, the solvent is or includes water, thereby providing an aqueous silver solution. The solvent can have any suitable degree of polarity, including highly polar, moderately polar or non-polar, or substantially or completely non-polar. The solvent typically has sufficient solvating power to solubilize the solution components. Some examples of water-based solvents include water and water-alcohol mixtures. Some examples of organic-based solvents include, but are not limited to, alcohols (e.g., methanol or ethanol), glycols (e.g., alkyl glycols), ketones, aldehydes, amines, tetrahydrofuran, nitrobenzene, nitrotoluene, glymes (e.g., glyme, diglyme and tetraglyme), and the like, and their combinations.

The concentration of silver ion in the impregnating solution is typically in the range from about 0.1% by weight to the maximum permitted by the solubility of the particular silver salt or complex employed. More typically, the concentration of silver ion is from about 0.5, 1, 2, or 5 wt % to 30, 35, 40, or 45 wt % by weight of the impregnating solution. Generally, in addition to silver ion, the impregnating solution used in the second stage impregnation contains one or more inorganic promoting species. The one or more promoting species can be any of those species, known in the art, that function to improve the activity or selectivity of the silver catalyst. The promoting species can be, for example, an alkali, alkaline earth, transition, or main group element, typically included in the form of a salt, e.g., lithium nitrate, cesium hydroxide, ammonium sulfate, and/or ammonium rhenate. The promoting species are included in the silver-containing solution of the second stage in order to deposit the promoting species along with silver ions into the carrier. In other embodiments, the impregnating solution in the second stage does not include a promoting species. However, in that case, promoting species are impregnated into the carrier by use of a separate solution containing the promoting species in a third stage impregnation or as a separate impregnating solution used in the first impregnation stage after incorporation of silver nanoparticles. In some embodiments, only silver, without promoters, is deposited in the first stage impregnation. In some embodiments, any promoters are deposited either during or after the second stage impregnation.

As used herein, a "promoting amount" of a promoting species refers to an amount that provides an improvement in one or more of the catalytic properties of the catalyst when compared to a catalyst not containing the promoting species. Examples of catalytic properties include, inter alia, selectivity, activity, stability, and operability (resistance to runaway). Moreover, it is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement is exhibited in the activity rather than in the selectivity. Generally, the promoting species are in an ionic form when deposited in the carrier.

In some embodiments, the produced catalyst may include a promoting amount of an alkali (Group 1) element or a mixture of two or more alkali elements. Some examples of alkali promoters include, for example, lithium, sodium, potassium, rubidium, cesium or combinations thereof. Cesium is often preferred, with combinations of cesium with other alkali elements also being preferred. The amount of alkali element will typically range from about 10 ppm to about 3000 ppm, more typically from about 15 ppm to about 2000 ppm, more typically from about 20 ppm to about 1500 ppm, and even more typically from about 50 ppm to about 1000 ppm by weight of the total catalyst, expressed in terms of the alkali element.

The produced catalyst may also or alternatively include a promoting amount of an alkaline earth (Group 2) element or a mixture of two or more alkaline earth elements. Some examples of alkaline earth promoters include, for example, beryllium, magnesium, calcium, strontium, and barium or combinations thereof. The amounts of alkaline earth promoters can be used in amounts similar to those used for the alkali or transition metal promoters.

The produced catalyst may also or alternatively include a promoting amount of a main group element or a mixture of two or more main group elements. Some examples of main group elements include the elements in Group 13 (boron group), Group 15 (phosphorous group), Group 16 (sulfur group), and Group 17 (halogen group) of the Periodic Table of the Elements. In some embodiments, the catalyst includes a promoting amount of at least one of sulfur, phosphorus, boron, halogen (e.g., fluorine), gallium, or a combination thereof. The main group element is generally present in ionic form, i.e., in the form of a salt or other compound.

The produced catalyst may also or alternatively include a promoting amount of one or more transition metals other than silver. Some examples of transition metals include elements of Group 3 (scandium group), Group 4 (titanium group), Group 5 (vanadium group), Group 6 (chromium group), Group 7 (manganese group), Group 8 (iron group), Group 9 (cobalt group), Group 10 (nickel group), Group 11 (copper group), and Group 12 (zinc group) of the Periodic Table of the Elements, as well as combinations thereof. More typically, the transition metal is an early transition metal, i.e., from Groups 3-7, such as, for example, hafnium, yttrium, molybdenum, tungsten, rhenium, chromium, titanium, zirconium, vanadium, tantalum, niobium, or a combination thereof. In one embodiment, the transition metal promoter is present in an amount from about 10 ppm to about 1000 ppm by weight of the catalyst. In another embodiment, the transition metal promoter is present in an amount from about 20 ppm to about 500 ppm by weight of the catalyst. In a further embodiment, the transition metal promoter is present in an amount from about 30 ppm to about 350 ppm by weight of the catalyst. Alternatively, the transition metal can be present in an amount of from about 0.1 micromoles per gram to about 10 micromoles per gram, more typically from about 0.2 micromoles per gram to about 5 micromoles per gram, and even more typically from about 0.5 micromoles per gram to about 4 micromoles per gram of the carrier or silver-containing catalyst, expressed in terms of the metal.

Of the transition metal promoters listed, rhenium (Re) is a particularly efficacious promoter for ethylene epoxidation high selectivity catalysts. The rhenium component in the carrier or catalyst can be in any suitable form, but is more typically one or more rhenium-containing compounds (e.g., a rhenium oxide) or complexes. The rhenium can be present in an amount of, for example, about 0.001 wt. % to about 1 wt. %. More typically, the rhenium is present in amounts of, for example, about 0.005 wt. % to about 0.5 wt. %, and even more typically, from about 0.01 wt. % to about 0.05 wt. % by weight of the catalyst, expressed as rhenium metal.

The produced catalyst may also include a promoting amount of a rare earth metal or a mixture of two or more rare earth metals, as a rare earth metal salt or complex. The rare earth metals include any of the elements having an atomic number of 57-103. Some examples of these elements include lanthanum (La), cerium (Ce), and samarium (Sm). The amount of rare earth metal promoters can be used in amounts similar to those used for the transition metal promoters.

After impregnation with silver and any promoters (e.g., one or more of Cs, Re, Li, W, F, P, Ga, and/or S), the impregnated carrier is removed from the solution and subjected to an elevated temperature for a time sufficient to reduce the ionic silver to metallic silver and to remove volatile decomposition products from the silver-containing support. The elevated temperature may be considered a calcination process, particularly when a temperature of 200° C. is used, but it may alternatively be considered a drying process if a temperature less than 200° C. is used. For convenience, the elevated temperature process is commonly referred to as a calcination process. The calcination, whether in the first or second stage, is typically accomplished by heating the impregnated carrier, preferably at a gradual rate, to a temperature in a range of about 200° C. to about 600° C., more typically from about 200° C. to about 500° C., more typically from about 250° C. to about 500° C., and more typically from about 200° C. or 300° C. to about 450° C., at a reaction pressure in a range from about 0.5 to about 35 bar. In general, the higher the temperature, the shorter the required calcination period. A wide range of heating periods has been described in the art for the thermal treatment of impregnated supports. Reference is made to, for example, U.S. Pat. No. 3,563,914, which indicates heating for less than 300 seconds, and U.S. Pat. No. 3,702,259, which discloses heating from 2 to 8 hours at a temperature of from 100° C. to 375° C. to reduce the silver salt in the catalyst. A continuous or step-wise heating program may be used for this purpose. During calcination, the impregnated support is typically exposed to a gas atmosphere comprising an inert gas, such as nitrogen. The inert gas may also include a reducing agent. After calcination, the amount of silver in the catalyst is typically at least 16, 17, 18, 19, or 20 wt %.

The produced catalyst preferably exhibits a selectivity of at least 85% for the conversion of ethylene to ethylene oxide. In different embodiments, the produced catalyst exhibits a selectivity of about or at least, for example, 85%, 86%, 87%, 88%, 89%, 90%, 91%, 92%, or 93%, or a selectivity within a range bounded by any two of the foregoing values.

The porous carrier may be selected from any of the solid refractory carriers known in the art for use in silver-based catalysts. Some examples of carrier materials include alumina (e.g., alpha-alumina), charcoal, pumice, magnesia, zirconia, titania, kieselguhr, fuller's earth, silicon carbide, silica, silicon carbide, clays, artificial zeolites, natural zeolites, silicon dioxide and/or titanium dioxide, ceramics, and combinations thereof.

In some embodiments, the carrier includes or is completely composed of alumina, which may be a single type of alumina (e.g., alpha-alumina) or a mixture of alumina compositions (e.g., gamma- and alpha-alumina). The alpha-alumina may be of a high purity, i.e., at least or greater than 95 wt % or 98 wt % alpha-alumina. The alpha-alumina carrier may or may not also include inorganic oxides other than alpha-alumina, such as silica, alkali metal oxides (e.g., sodium oxide) and trace amounts of other metal-containing or non-metal-containing additives or impurities.

The carrier precursor particles can be of any suitable size, and are typically microparticles. In typical embodiments, the carrier microparticles have a particle size (i.e., diameter, if substantially spherical) within a range of about 40-100 microns (μm), which typically includes a primary particle size of about 1-5 microns. The carrier precursor particles may also be composed of two or more portions of microparticles of different sizes or size ranges, such as a first portion having an average size in the range of 20-100 microns and a second portion having an average size in the range of 1-10 microns. Moreover, each portion of the carrier precursor particles may be in a suitable weight percentage by total weight of carrier precursor or finished carrier (before silver impregnation).

The carrier may be produced by conventional techniques well known to those skilled in the art, such as by combining alumina microparticles, a solvent (e.g., water), a temporary binder or burnout material, a permanent binder, and/or a porosity controlling agent, and then shaping, molding, or extruding the resulting paste, before firing (i.e., calcining) the preform by methods well known in the art. Temporary binders, or burnout materials, include cellulose, substituted celluloses, e.g., methylcellulose, ethylcellulose, and carboxyethylcellulose, stearates (such as organic stearate esters, e.g., methyl or ethyl stearate), waxes, granulated polyolefins (e.g., polyethylene and polypropylene), walnut shell flour, and the like, which are decomposable at the temperatures employed. The binders are responsible for imparting porosity to the carrier material. Burnout material is used primarily to ensure the preservation of a porous structure during the green (i.e., unfired phase) in which the mixture may be shaped into particles by molding or extrusion processes. Burnout materials are essentially completely removed during the firing to produce the finished carrier. Alternatively, the carrier may be purchased from a catalyst carrier provider. Some specific carrier formulations and methods for their preparation are described in U.S. Pat. No. 8,791,280, the contents of which are herein incorporated by reference in their entirety.

The formed paste is extruded or molded into the desired shape and fired at a temperature typically from about 1200° C. to about 1600° C. to form the carrier. In embodiments in which the particles are formed by extrusion, it may be desirable to include conventional extrusion aids. Generally, the performance of the carrier is enhanced if it is treated by soaking the carrier in a solution of an alkali hydroxide, such as sodium hydroxide, potassium hydroxide, or an acid such as $HNO_3$, as described in U.S. Pat. No. 7,507,844. After treatment, the carrier is preferably washed, such as with water, to remove unreacted dissolved material and treating solution, and then optionally dried.

The carrier typically has a B.E.T. surface area of up to 20 $m^2/g$. The B.E.T. surface area is more typically in the range of about 0.1 to 10 $m^2/g$, and more typically from 1 to 5 $m^2/g$. In other embodiments, the carrier is characterized by a B.E.T. surface area of about 0.3 $m^2/g$ to about 3 $m^2/g$, or a surface area of about 0.6 $m^2/g$ to about 2.5 $m^2/g$, or a surface area of about 0.7 $m^2/g$ to about 2.0 $m^2/g$. The B.E.T. surface area described herein can be measured by any suitable method, but is more preferably obtained by the method described in Brunauer, S., et al., *J. Am. Chem. Soc.*, 60, 309-16 (1938). The final carrier typically possesses a water absorption value (water pore volume) ranging from about 0.10 cc/g to about 0.80 cc/g, more typically from about 0.2 cc/g to about 0.8 cc/g, and more typically from about 0.25 cc/g to about 0.6 cc/g.

The carrier can have any suitable distribution of pore diameters. As used herein, the term "pore diameter" is meant to indicate a pore size. The pore volume (and pore size distribution) described herein can be measured by any suitable method, such as by the conventional mercury porosimeter method described in, for example, Drake and Ritter, *Ind. Eng. Chem. Anal. Ed.*, 17, 787 (1945). Typically, the pore diameters are at least about 0.01 microns (0.01 μm), and more typically, at least about 0.1 μm. Typically, the pore diameters are no more than or less than about 10, 15, 20, 25, 30, 35, 40, 45, or 50 μm. In different embodiments, the pore diameters are about, at least, above, up to, or less than, for example, 0.2 μm, 0.5 μm, 1.0 μm, 1.2 μm, 1.5 μm, 1.8 μm, 2.0 μm, 2.5 μm, 3 μm, 3.5 μm, 4 μm, 4.5 μm, 5 μm, 5.5 μm, 6 μm, 6.5 μm, 7 μm, 7.5 μm, 8 μm, 8.5 μm, 9 μm, 9.5 μm, 10 μm, or 10.5 μm, or the pore diameters are within a range bounded by any two of the foregoing exemplary values. Any range of pore sizes, as particularly derived from any of the above exemplary values, may also contribute any suitable percentage of the total pore volume, such as at least, greater than, up to, or less than, for example, 1, 2, 5, 10, 15, 20, 25, 30, 40, 50, 60, 70, 80, 90, 95, or 98% of the total pore volume. In some embodiments, a range of pore sizes may provide the total (i.e., 100%) pore volume.

In some embodiments, the carrier possesses a multimodal pore size distribution within any of the pore size ranges described above. The multimodal pore size distribution can be, for example, bimodal, trimodal, or of a higher modality. The multimodal pore size distribution is characterized by the presence of different pore sizes of peak concentration (i.e., different peak pore sizes) in a pore size vs. pore volume distribution plot. The different peak pore sizes are preferably within the range of pore sizes given above. Each peak pore size can be considered to be within its own pore size distribution (mode), i.e., where the pore size concentration on each side of the distribution falls to approximately zero (in actuality or theoretically). In one embodiment, different pore size distributions, each having a peak pore size, are non-overlapping by being separated by a volume concentration of pores of approximately zero (i.e., at baseline). In another embodiment, different pore size distributions, each having a peak pore size, are overlapping by not being separated by a volume concentration of pores of approximately zero. Each mode of pores may contribute any suitable percentage of the total pore volume, such as any of the percentages or ranges thereof, provided above.

The macroscale shape and morphology of the carrier, i.e., after compounding and calcining of the carrier particles, can be any of the numerous shapes and morphologies known in the art. For example, the carrier can be in the form of particles, chunks, pellets, rings, spheres, three-holes, wagon wheels, cross-partitioned hollow cylinders, and the like, of a size preferably suitable for employment in fixed-bed epoxidation reactors. In particular embodiments, the macroscopic carrier units may have equivalent diameters of about, for example, 1, 2, 3, 4, 5, 6, 7, 8, 9, 10, 11, 12, 13, 14, or 15 mm, or an equivalent diameter within a range bounded by any two of the foregoing exemplary values. As known in the art, the term "equivalent diameter" is used to express the size of an irregularly-shaped object by expressing the size of the object in terms of the diameter of a sphere having the same volume as the irregularly-shaped object. The equivalent diameter is preferably compatible with the internal diameter of the tubular reactors in which the catalyst is placed. Alternatively, the equivalent diameter is the diameter of a sphere having the same external surface area (i.e., neglecting surface area within the pores of the particle) to volume ratio as the carrier units being employed.

In another aspect, the instant disclosure is directed to a method for the vapor phase conversion of ethylene to ethylene oxide in the presence of oxygen by use of the catalyst described above. Typically, after calcining the high selectivity catalyst, the calcined catalyst is loaded into reactor tubes of an epoxidation reactor, typically a fixed bed tubular reactor, utilizing conventional loading methods well known to those skilled in the art. After loading, the catalyst bed may be swept by passing an inert gas such as nitrogen over the catalyst bed.

The inventive catalysts are particularly active and selective in the conversion of ethylene to ethylene oxide. The conditions for conducting such an oxidation reaction are well known in the art. This applies, for example, to suitable temperatures, pressures, residence times, diluent materials (e.g., nitrogen, carbon dioxide, steam, argon, methane or other saturated hydrocarbons), the presence or absence of moderating agents to control the catalytic action (e.g., 1, 2-dichloroethane, vinyl chloride or ethyl chloride), the desirability of employing recycle operations or applying successive conversion in different reactors to increase the yields of ethylene oxide, and other particular conditions that may be beneficial for converting ethylene to ethylene oxide. Molecular oxygen employed as a reactant may be obtained from conventional sources, and may be relatively pure oxygen, or a concentrated oxygen stream comprising oxygen in a major amount with lesser amounts of one or more diluents, such as nitrogen or argon, or air.

Generally, the ethylene oxide production process is conducted by continuously contacting an oxygen-containing gas with ethylene in the presence of the catalyst at a temperature in the range from about 180° C. to about 330° C., more typically from about 200° C. to about 325° C., and more typically from about 225° C. to about 270° C., at a pressure which may vary from about atmospheric pressure to about 30 atmospheres depending on the mass velocity and productivity desired. Pressures in the range of from about atmospheric to about 500 psi are generally employed. Higher pressures may, however, be employed within the scope of this disclosure. Residence times in large-scale reactors are generally on the order of about 0.1 to about 5 seconds. A typical process for the oxidation of ethylene to ethylene oxide comprises the vapor phase oxidation of ethylene with molecular oxygen in the presence of the inventive catalyst in a fixed bed, tubular reactor. Conventional commercial fixed bed ethylene oxide reactors are typically in the form of a plurality of parallel elongated tubes (in a suitable shell). In one embodiment, the tubes are approximately 0.7 to 2.7 inches O.D. and 0.5 to 2.5 inches I.D. and 15-45 feet long filled with catalyst.

In the production of ethylene oxide, reactant feed mixtures typically contain from about 0.5 to about 45% ethylene and from about 3 to about 15% oxygen, with the balance comprising comparatively inert materials, including such substances as nitrogen, carbon dioxide, methane, ethane, argon and the like. Only a portion of the ethylene is typically reacted per pass over the catalyst. After separation of the desired ethylene oxide product and removal of an appropriate purge stream and carbon dioxide to prevent uncontrolled build up of inert products and/or by-products, unreacted materials are typically returned to the oxidation reactor. For purposes of illustration only, the following are conditions that may be used in a conventional industrial ethylene oxide reactor unit: a gas hourly space velocity (GHSV) of 1500-10,000 $h^{-1}$, a reactor inlet pressure of 150-400 psig, a coolant temperature of 180-315° C., an oxygen conversion level of 10-60%, and an EO production (work rate) of 100-300 kg EO per cubic meters of catalyst per hour. Typically, the feed composition at the reactor inlet comprises 1-40% ethylene, 3-12% oxygen, 0.3-40% $CO_2$, 0-3% ethane, 0.3-20 ppmv total concentration of organic chloride moderator, with the balance of the feed being argon, methane, nitrogen, or mixtures thereof.

Some examples of organic chloride moderators that can be employed in the present disclosure include, for example, organic halides, such as $C_1$ to $C_8$ halohydrocarbons, which, may be, for example, methyl chloride, ethyl chloride, ethylene dichloride, vinyl chloride, or a mixture thereof. Also suitable are hydrogen-free chlorine sources, such as perhalogenated hydrocarbons and diatomic chlorine, both of which are particularly effective as moderators in gas phase epoxidation. Perhalogenated hydrocarbons refer to organic molecules in which all of the hydrogen atoms in a hydrocarbon have been substituted with halogen atoms. Some examples of perhalogenated hydrocarbons include trichlorofluoromethane and perchloroethylene. The concentration of the moderator should be controlled so as to balance a number of competing performance characteristics. For example, moderator concentration levels that result in improved activity may simultaneously lower selectivity. Controlling moderator concentration level is particularly important with rhenium-containing catalysts of the present disclosure, because as the rhenium-containing catalysts age, the moderator concentration must be carefully monitored so as to continually increase, within small increments, since optimal selectivity values are obtained only within a narrow moderator concentration range.

In other embodiments, the process of ethylene oxide production includes the addition of oxidizing gases to the feed to increase the efficiency of the process. For example, U.S. Pat. No. 5,112,795 discloses the addition of 5 ppm of nitric oxide to a gas feed having the following general composition: 8 volume % oxygen, 30 volume % ethylene, about 5 ppmw ethyl chloride, with the balance as nitrogen.

The ethylene oxide, as produced, is separated and recovered from the reaction products using methods well known in the art. The ethylene oxide process may include a gas recycle process wherein a portion or substantially all of the reactor effluent is readmitted to the reactor inlet after substantially removing the ethylene oxide product and byproducts. In the recycle mode, carbon dioxide concentrations in the gas inlet to the reactor may be, for example, about 0.3 to about 6 volume percent, and more typically, about 0.3 to about 2.0 volume percent.

Examples have been set forth below for the purpose of further illustrating the invention. The scope of this invention is not to be in any way limited by the examples set forth herein.

EXAMPLES

Example 1. Conventional Preparation of a Silver-Containing Catalyst (Comparative)

An alumina carrier was impregnated with a water-based impregnation solution containing silver in the form of silver-amine oxalate and catalytically active amounts of promoters in soluble forms. The amount of silver deposited on the carrier was about 16.5 wt %. After impregnation, the carrier was calcined under standard conditions.

Example 2. Preparation of a Silver-Containing Catalyst (According to the Invention)

A carrier was first impregnated with a water-based impregnation solution containing silver in the form of silver-amine oxalate to achieve a silver concentration on the carrier of 0.18 wt % after calcination under conventional conditions. In a second impregnation, silver was co-impregnated with catalytically active amounts of promoters in soluble form. The total amount of silver deposited on the carrier after the second impregnation was about 16.5 wt %. After the second impregnation, the carrier was calcined under standard conditions.

Example 3. Preparation of a Silver-Containing Catalyst without Promoters

A carrier was impregnated with a water-based impregnation solution containing silver in the form of silver-amine oxalate but without any amounts of promoters in soluble forms. The total amount of silver deposited on the carrier was about 16.5 wt %. After impregnation, the material was calcined under standard conditions.

Example 4. Performance Testing of Catalysts Prepared in Examples 1 and 2

The catalysts prepared according to Examples 1 and 2 were tested for their catalytic performance, and the results are shown in Table 1 below. From the results in Table 1, it is clear that the catalyst prepared according to the invention (i.e., Example 2), which employed a small amount of silver pre-deposited before a conventional silver impregnation and calcination, exhibits an improved selectivity, activity, and activity stability.

TABLE 1

Selectivity, activity, and stability for catalysts made on carriers with and without an initial low silver (Ag) deposition.

| Catalyst Preparation | $S_{500\,h}$, % | $S_{1000\,h}$, % | $S_{1500\,h}$, % | $T_{500\,h}$, °C. | $T_{1000\,h}$, °C. | $T_{1500\,h}$, °C. |
|---|---|---|---|---|---|---|
| Without initial low Ag deposition (Example 1) | 88.9 | 89.3 | 88.7 | 247.6 | 249.6 | 254.4 |
| With initial low Ag deposition (Example 2) | 89.2 | 89.5 | 89.9 | 240.3 | 244.3 | 247.7 |

Example 5. XPS Analysis of Catalysts Prepared in Examples 1, 2, and 3

The catalysts prepared according to Examples 1, 2, and 3 were analyzed by x-ray photoelectron spectroscopy (XPS) to determine the near surface silver concentration in atomic %. The results are shown in Table 2 below.

TABLE 2

Silver near surface concentration in atomic % of catalysts

| Catalyst Preparation | Ag deposition in a first impregnation | Final Ag in composition, % | Ag, atomic % | Loss of Ag signal, % |
|---|---|---|---|---|
| Example 1 | 0 | 16.33 | 20.6 | 8.4 |
| Example 2 | 0.18 | 16.58 | 13.8 | 38.7 |
| Example 3 | 0 | 15.74 | 22.5 | 0 |

Table 2, above, shows the silver near surface concentration in atomic % from XPS analysis of the catalyst prepared by conventional single impregnation (Example 1), after double impregnation with 0.18 wt % silver deposition in the first step (Example 2), and comparison sample impregnated with nominal 16 wt % silver but without any promoters (Example 3). The results in Table 2 establish that the near surface silver concentration decreases more after the inventive double impregnation process using an initial 0.18 wt % silver deposition, as described in Example 2.

As the XPS silver signal diminishes with increasing coverage of promoters, the results in Table 2 indicate that the two-stage impregnation process, as exemplified in Example 2, results in greater coverage of the silver nanoparticles or overall total silver by promoters than the conventional process, as exemplified in Example 1. Thus, as the catalyst prepared according to Example 2 (of the invention) exhibits an improved selectivity, activity, and activity stability compared to a catalyst prepared by a conventional process (i.e., Example 1), the totality of the results suggest that the improved performance is due at least in part to the greater coverage of promoters on silver afforded by the inventive two-stage impregnation process.

Example 6. SEM Analysis of Carriers and Resulting Catalysts Prepared in Examples 1 and 2

Figure 1B:
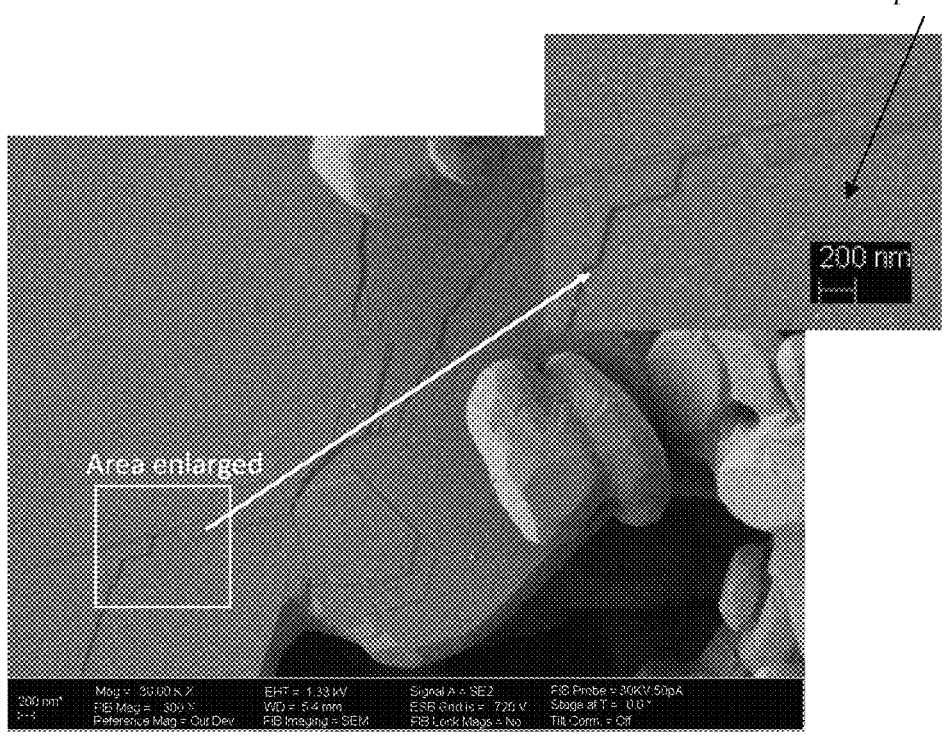

FIG. 1A is an SEM (scanning electron microscopy) image taken at 30KX magnification of an alumina carrier before any deposition of silver. FIG. 1B is an SEM image of the alumina carrier after deposition of 0.18 wt % Ag, as described in Example 2. Notably, FIG. 1B shows only small silver metal particles (nanoparticles) on the carrier surface. The SEM images were taken at 30KX magnification.

Figure 2A:
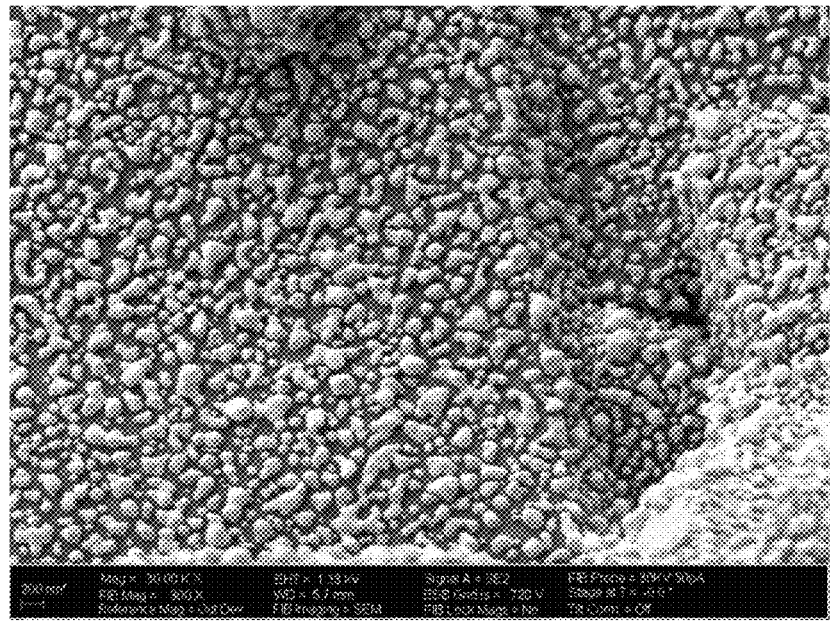
FIGS. 2A, 2B.
Figure 2B:
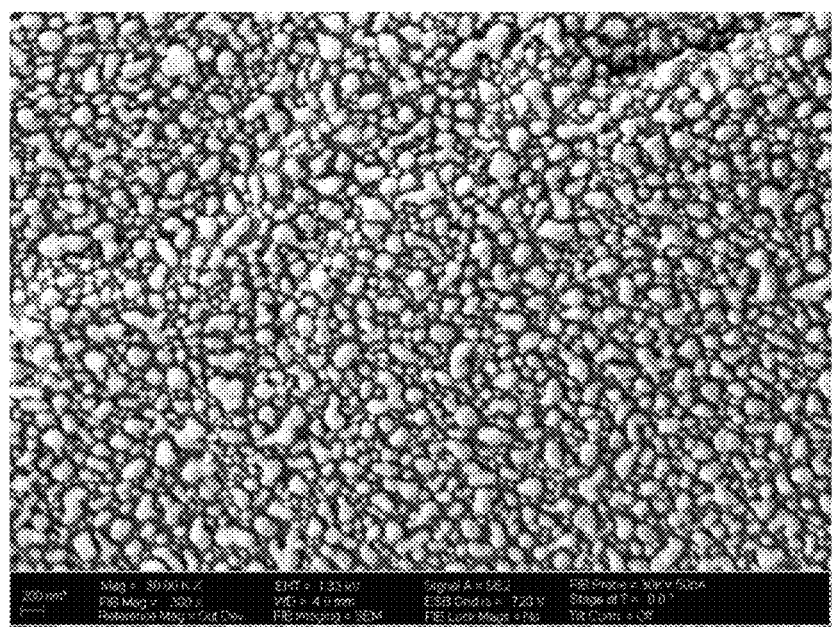

FIG. 2A is an SEM image taken at 30KX magnification of the HSC catalyst prepared in Example 1 by single-step deposition of silver and promoters, with total deposited silver of 16.3 wt %. FIG. 2B is an SEM image of the HSC catalyst prepared in Example 2 after a first low silver impregnation followed by a second (conventional) silver impregnation with silver and promoters, with total deposited silver of 16.6 wt %. Notably, the approximately same total silver loading apparently produces the same size and distribution of silver. Yet, surprisingly, the inventive catalyst produced according to Example 2 exhibits an improved performance.

While there have been shown and described what are presently believed to be the preferred embodiments of the present disclosure, those skilled in the art will realize that other and further embodiments can be made without departing from the spirit and scope of the present disclosure, and this disclosure includes all such modifications that are within the intended scope of the claims set forth herein.

What is claimed is:

1. A method for producing a catalyst effective in the oxidative conversion of ethylene to ethylene oxide, the method comprising:
   (i) impregnating a porous refractory carrier with an initial amount of silver ion in a range of 0.1 wt % to 0.5 wt % of silver per total weight of the refractory carrier and silver, and at least partially reducing said silver ion to elemental silver to produce a low-silver catalyst precursor having isolated silver atoms or silver nanoparticles having a size less than 10 nm in diameter on surfaces of said refractory carrier, wherein said low-silver catalyst precursor contains elemental silver on the refractory carrier in said initial amount of 0.1 wt % to 0.5 wt % of silver per total weight of the refractory carrier and silver; and
   (ii) impregnating the low-silver catalyst precursor with a catalytic amount of silver ion of at least 10 wt % total amount of silver per total weight of the refractory carrier and silver, and also impregnating the low-silver catalyst precursor with at least one inorganic promoting species that promotes the oxidative conversion of ethylene to ethylene oxide and that is included in a catalytically promoting amount, and subjecting the refractory carrier having a catalytic level of silver ion to a calcination process in which the refractory carrier having a catalytic level of silver ion is subjected to an elevated temperature of at least 200° C. to completely reduce silver ion to elemental silver in said refractory carrier, to produce said catalyst effective in the oxidative conversion of ethylene to ethylene oxide.

2. The method of claim 1, wherein said sub-catalytic level of silver is in a range of 0.1 wt % to 0.3 wt % of silver per total weight of the refractory carrier and silver.

3. The method of claim 1, wherein said silver nanoparticles in step (i) have a size of up to 5 nm in diameter.

4. The method of claim 1, wherein said silver nanoparticles in step (i) have a size of up to 2 nm in diameter.

5. The method of claim 1, wherein said initial amount of silver ion in step (i) is at least partially reduced to elemental silver by subjecting the refractory carrier in step (i) to an elevated temperature of at least 100° C.

6. The method of claim 1, wherein said at least one inorganic promoting species is selected from the group consisting of alkali, alkaline earth, main group, and transition metal elements other than silver.

7. The method of claim 1, wherein said at least one inorganic promoting species is selected from the group consisting of cesium (Cs), lithium (Li), tungsten (W), fluorine (F), phosphorus (P), gallium (Ga), rhenium (Re), and sulfur (S).

8. The method of claim 1, wherein said at least one inorganic promoting species is selected from the group consisting of Re, Cs, and Li.

9. The method of claim 1, wherein said at least one inorganic promoting species comprises Re.

10. The method of claim 1, wherein said catalytic amount of silver in step (ii) is a catalytic amount of silver of at least 15 wt %.

11. The method of claim 1, wherein the refractory carrier is comprised of an alumina.

12. The method of claim 1, wherein said catalyst effective in the oxidative conversion of ethylene to ethylene oxide, as produced in step (ii), exhibits at least one of an improved catalyst activity, selectivity, and stability, compared to a catalyst produced by impregnating the refractory carrier with said catalytic amount of silver ion of at least 10 wt % and said at least one inorganic promoting species in a single impregnation step, without step (i), followed by calcination at said elevated temperature of at least 200° C.

13. The method of claim 1, wherein said catalyst effective in the oxidative conversion of ethylene to ethylene oxide, as produced in step (ii), possesses a greater coverage of said at least one inorganic promoting species on said elemental silver, compared to a catalyst produced by impregnating the refractory carrier with said catalytic amount of silver ion of at least 10 wt % and said at least one inorganic promoting species in a single impregnation step, without step (i), followed by calcination at said elevated temperature of at least 200° C.

14. The method of claim 1, wherein the refractory carrier is impregnated with said initial amount of silver in step (i) by contacting the porous refractory carrier with a silver-containing solution containing the initial amount of silver in the form of a silver salt under conditions where the silver-containing solution becomes infused into the porous refractory carrier.

15. The method of claim 1, wherein the low-silver catalyst precursor is impregnated with said catalytic amount of silver in step (ii) by contacting the low-silver catalyst precursor with a silver-containing solution containing the catalytic level of silver in the form of a silver salt under conditions where the silver-containing solution becomes infused into the porous refractory carrier.

16. A low-silver catalyst precursor comprising a porous refractory carrier and a level of silver in a range of 0.1 wt % to 0.5 wt % of silver per total weight of the refractory carrier and silver, wherein said silver comprises isolated silver atoms or silver nanoparticles having a size less than 10 nm in diameter on surfaces of said refractory carrier.

17. The catalyst precursor of claim 16, wherein said sub-catalytic level of silver is in a range of 0.1 wt % to 0.3 wt % of silver per total weight of the refractory carrier and silver.

18. The catalyst precursor of claim 16, wherein said nanoparticles have a size of up to 5 nm in diameter.

19. The catalyst precursor of claim 16, wherein said silver nanoparticles have a size of up to 2 nm in diameter.

20. The catalyst precursor of claim 16, wherein said porous refractory carrier is comprised of an alumina.

* * * * *